United States Patent
Salter et al.

(10) Patent No.: US 10,466,195 B2
(45) Date of Patent: Nov. 5, 2019

(54) VEHICLE WINDOW HAVING MOISTURE SENSOR

(71) Applicant: Ford Global Technologies, LLC, Dearborn, MI (US)

(72) Inventors: Stuart C. Salter, White Lake, MI (US); Paul Kenneth Dellock, Northville, MI (US); Pietro Buttolo, Dearborn Heights, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 205 days.

(21) Appl. No.: 15/458,304

(22) Filed: Mar. 14, 2017

(65) Prior Publication Data
US 2018/0266978 A1   Sep. 20, 2018

(51) Int. Cl.
*G01N 27/22* (2006.01)
*B32B 17/10* (2006.01)
*B60J 1/00* (2006.01)
*B60S 1/02* (2006.01)
*G01D 5/24* (2006.01)

(52) U.S. Cl.
CPC ..... *G01N 27/223* (2013.01); *B32B 17/10385* (2013.01); *B32B 17/10724* (2013.01); *B60J 1/002* (2013.01); *B60S 1/026* (2013.01); *G01D 5/24* (2013.01); *B32B 2250/03* (2013.01); *B32B 2307/202* (2013.01); *B32B 2307/204* (2013.01); *B32B 2605/08* (2013.01)

(58) Field of Classification Search
CPC ............ G01N 27/223; B32B 17/10385; B32B 17/10724; B32B 2250/03; B32B 2307/202; B32B 2307/204; B32B 2605/08; B60H 1/00; B60J 1/002; B60S 1/026; G01D 5/24
USPC ...................................... 454/75, 93, 95, 121
See application file for complete search history.

(56) References Cited

U.S. PATENT DOCUMENTS

| | | | |
|---|---|---|---|
| 5,526,294 A | | 6/1996 | Ono et al. |
| 5,751,071 A | * | 5/1998 | Netzer .................... B60S 1/026 219/203 |
| 5,880,538 A | | 3/1999 | Schulz |

(Continued)

OTHER PUBLICATIONS

U.S. Appl. No. 15/404,525, filed Jan. 12, 2017, 15 pages of specification, 5 pages of drawings and 3 pages of Official Filing Receipt.

(Continued)

*Primary Examiner* — Gregory L Huson
*Assistant Examiner* — Dana K Tighe
(74) *Attorney, Agent, or Firm* — Vichit Chea; Price Heneveld LLP (57) ABSTRACT

A proximity switch and moisture sensing assembly includes a vehicle window and a proximity switch including a proximity sensor located on the window and providing an activation field. The proximity switch and moisture sensing assembly also includes control circuitry monitoring a signal responsive to the activation field, determining a switch activation based on the signal, and determining a moisture value based upon the signal. A conductive shield may be disposed between the proximity sensors and the outside environment to reduce the effects of moisture on the outer side of the window.

18 Claims, 11 Drawing Sheets

(56) References Cited

U.S. PATENT DOCUMENTS

| | | |
|---|---|---|
| 7,296,461 B2 * | 11/2007 | Barguirdjian ..... B32B 17/10036 |
| | | 73/73 |
| 9,219,472 B2 | 12/2015 | Buttolo et al. |
| 9,287,864 B2 | 3/2016 | Buttolo et al. |
| 9,371,032 B2 | 6/2016 | Veerasamy |
| 2006/0082545 A1 | 4/2006 | Choquet et al. |
| 2006/0207325 A1 * | 9/2006 | Kataoka ............. G01N 21/4738 |
| | | 73/335.01 |
| 2007/0235549 A1 * | 10/2007 | Nakajima .......... B60H 1/00785 |
| | | 236/44 R |
| 2008/0223127 A1 * | 9/2008 | Schmitt ................ B60S 1/0822 |
| | | 73/170.17 |
| 2011/0050589 A1 * | 3/2011 | Yan ....................... B60K 37/06 |
| | | 345/173 |
| 2011/0212279 A1 * | 9/2011 | Lemmer ............. C03C 17/3435 |
| | | 428/34 |
| 2012/0055557 A1 | 3/2012 | Belz et al. |
| 2013/0024169 A1 | 1/2013 | Veerasamy |
| 2014/0210592 A1 * | 7/2014 | Van Wiemeersch ..... G05B 1/01 |
| | | 340/5.61 |

OTHER PUBLICATIONS

"Touch Sensors Design Guide" by ATMEL, 10620 D-AT42-04/09, Revised Apr. 2009, 72 pages, Copyrighted 2008-2009 Atmel Corporation.

\* cited by examiner

VEHICLE WINDOW HAVING MOISTURE SENSOR

FIELD OF THE INVENTION

The present invention generally relates to proximity switches and sensors, and more particularly relates to vehicle glass mounted proximity switches and moisture sensing on a vehicle.

BACKGROUND OF THE INVENTION

Automotive vehicles are commonly equipped with various user actuatable input devices for entering inputs to control devices or functions. For example, keypads are often provided on the vehicle body exterior to enable a user to enter a sequence of inputs as a code to actuate a door lock without a mechanical key or key fob. Conventional keypads employed on motor vehicles typically include mechanical switches actuatable by users. It would be desirable to provide for an enhanced assembly that is economical and offers enhanced and reliable performance.

Climate control systems employed on board vehicles may include a humidity sensor for sensing humidity or moisture in the air within the vehicle such as near the window glass. The humidity may cause moisture buildup on the window and the climate control system may respond to reduce the moisture buildup. It may be desirable to provide for an enhanced proximity switch arrangement that reduces the need for a separate sensor to detect moisture within the vehicle.

SUMMARY OF THE INVENTION

According to one aspect of the present invention, a window having moisture sensing is provided. The window having moisture sensing includes a transparent medium having first and second surfaces, and a capacitive sensor disposed on the transparent medium for sensing moisture on the first surface. The window also includes a conductive shield provided between the capacitive sensor and the second surface of the transparent medium, the conductive shield reducing sensitivity of the sensor to moisture on the second surface.

Embodiments of the first aspect of the invention can include any one or a combination of the following features:
the transparent medium comprises a glass structure;
the glass structure comprises a first glass layer and a second glass layer, wherein the capacitive sensor is located between the first and second glass layers;
the capacitive sensor senses moisture based on amplitude of the signal;
the moisture is determined by comparing the amplitude of the signal to known moisture values in a look-up table;
the capacitive sensor further operates as a capacitive switch for a keypad assembly to control operation of a door lock to lock or unlock a vehicle door;
the first surface is an interior surface and the second surface is an exterior surface;
the window further has a defogger for defogging the interior surface of the window based on the sensed moisture;
control circuitry detects a user gesture input to the sensor and controls the defogger based on the user gesture input;
the conductive shield is formed of a conductive grid comprising an array of horizontal and conductive lines;
the conductive shield is formed of a substantially transparent conductive material;
the transparent conductive material comprises indium tin oxide; and
the conductive grid is disposed between the capacitive sensor and the second glass layer.

According to another aspect of the present invention, a vehicle window having moisture sensing is provided. The vehicle window having moisture sensing includes a glass structure having interior and exterior surfaces, and a capacitive sensor disposed on the glass structure for sensing moisture on the interior surface. The vehicle window also includes a conductive shield provided between the capacitive sensor and the exterior surface of the glass structure, the conductive grid reducing sensitivity of the sensor to moisture on the exterior surface.

Embodiments of the second aspect of the invention can include any one or a combination of the following features:
the glass structure comprises a first glass layer and a second glass layer, wherein the capacitive sensor is located between the first and second glass layers;
the capacitive sensor senses moisture based on amplitude of the signal;
the moisture is determined by comparing the amplitude of the signal to known moisture values in a look-up table;
the capacitive sensor further operates as a capacitive switch for a keypad assembly to control operation of a door lock to lock or unlock a vehicle door;
the window further has a defogger for defogging the interior surface of the window based on the sensed moisture; and
the conductive shield is formed of a conductive grid comprising an array of horizontal and conductive lines.

These and other aspects, objects, and features of the present invention will be understood and appreciated by those skilled in the art upon studying the following specification, claims, and appended drawings.

DETAILED DESCRIPTION OF THE PREFERRED EMBODIMENTS

Figure 1:
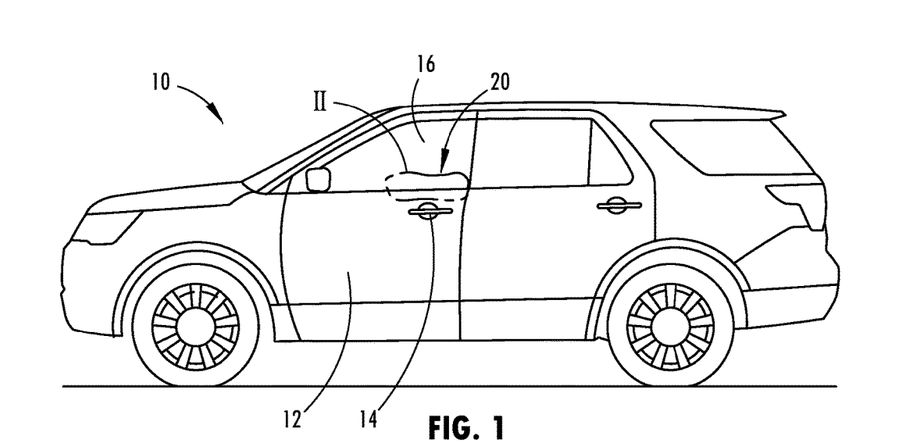
FIG. 1 is a side view of a motor vehicle window equipped with a capacitive proximity switch and moisture sensing assembly, according to one embodiment.
Figure 2:
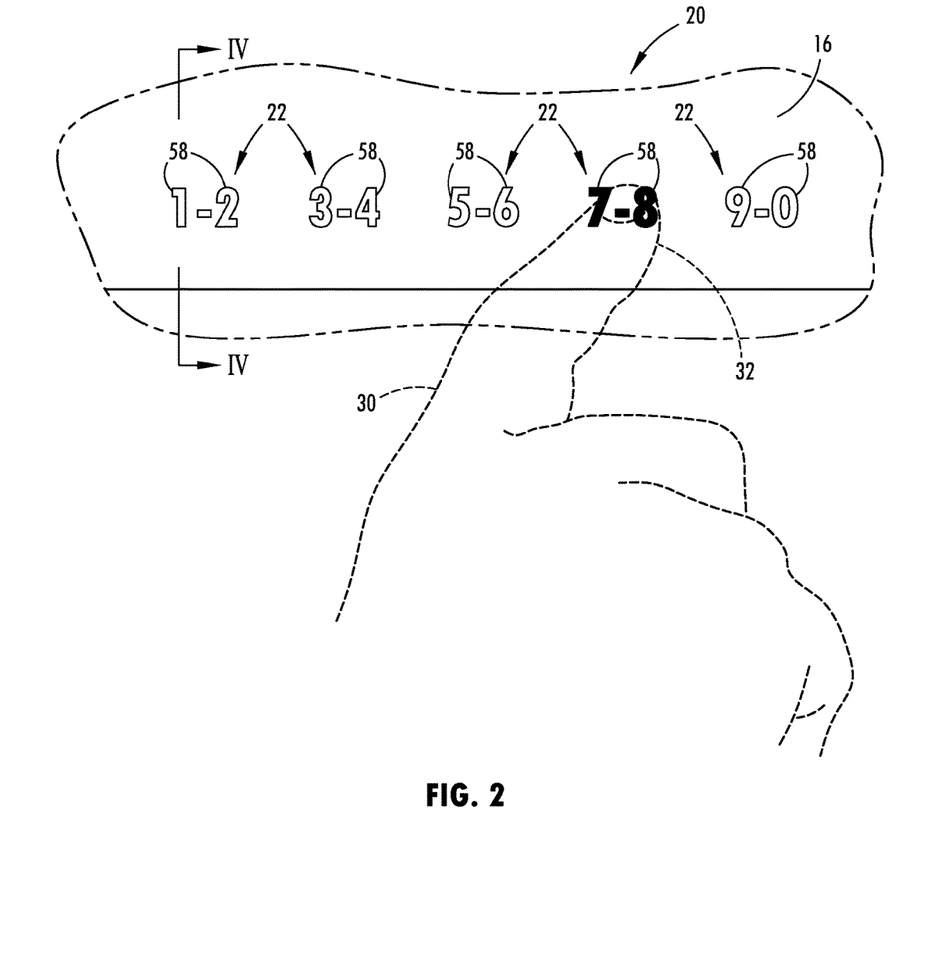
FIG. 2 is an enlarged view of section II of FIG. 1 further illustrating the capacitive proximity switch and moisture sensing assembly.

For purposes of description herein, the terms "upper," "lower," "right," "left," "rear," "front," "vertical," "horizontal," and derivatives thereof shall relate to the invention as oriented in FIGS. 1 and 2. However, it is to be understood that the invention may assume various alternative orientations, except where expressly specified to the contrary. It is also to be understood that the specific devices and processes illustrated in the attached drawings, and described in the following specification are simply exemplary embodiments of the inventive concepts defined in the appended claims. Hence, specific dimensions and other physical characteristics relating to the embodiments disclosed herein are not to be considered as limiting, unless the claims expressly state otherwise.

Referring to FIGS. 1 and 2, a wheeled motored vehicle 10 is generally illustrated having a capacitive proximity switch and moisture sensing assembly 20 shown configured as a vehicle door access keypad assembly that enables a person to enter a sequence of inputs to lock and unlock the vehicle doors, according to one embodiment. The vehicle 10 includes a passenger door 12 provided on the vehicle body and a door latch lock assembly 14 positioned on the door 12. The door latch lock assembly 14 may be actuatable by a person to unlatch and thereby open the door 12 and to lock and unlock the door 12 and other doors on the vehicle to control access to the vehicle 10. It should be appreciated that a driver may actuate a door lock switch in the vehicle and may also be equipped with a key fob that may remotely lock and unlock the door latch lock assembly 14 of vehicle door 12. The capacitive proximity switch and moisture sensing assembly 20 includes a plurality of proximity switches configured with user selectable proximity switches 22 (FIG. 2) forming a keypad to enable a person to input a code as a sequence of inputs to lock and unlock the vehicle door 12 by entering a programmed sequence of input characters (e.g., numbers) via pads 22 labelled with the identifier characters.

The proximity switch and moisture sensing assembly 20 is illustrated further in FIG. 2 having the plurality of user selectable proximity switches 22 shown arranged horizontally in the driver side door window 16, according to one embodiment. The proximity switches 22 are configured as a user input keypad. The proximity switches 22 include fluorescent patterns in the form of keypad indication characters 58 that are illuminable with light of a certain wavelength to display a lighted character image that is viewable on the outside surface of the window 16. The proximity switches 22 are user input keypads that each define a region upon which a user may touch the proximity switch with a finger or come in close proximity thereto to provide an input selection. The lighted characters 58 may be formed of a fluorescent ink, such as a security ink, that is essentially transparent and non-viewable in normal ambient lighting conditions. As such, the characters 58 are essentially invisible to a person until illuminated with light of a certain wavelength such as ultraviolet (UV) and/or infrared (IR) light. The characters 58 shown include numerical characters one and two (1•2) for the first proximity switch, numerical characters three and four (3•4) for the second proximity switch, numerical characters five and six (5•6) for the third proximity switch, numerical characters seven and eight (7•8) for the fourth proximity switch, and numerical characters nine and zero (9•0) for the fifth proximity switch. It should be appreciated that other characters such as letters or symbols may be employed as proximity switch identifiers. Each of the proximity switches 22 has a capacitive sensor that senses contact or close proximity (e.g., 1 millimeter) of the user's finger with a touch region of the proximity switch 22 and defines a binary switch output (on or off) indicative a user selection of that corresponding proximity switch.

The proximity switches 22 each include a proximity sensor positioned within the glass window for sensing close proximity of a user, such as a user's finger, in relation to the proximity switch. When a user 30, such as a user's finger 32, is detected in close proximity to one of the proximity switches, all of the proximity switches 22 may be lighted a green first color, according to one example, by the light source illuminating UV or IR radiation onto the fluorescent patterns 58 and thus viewable to a user. The illumination of all of the proximity switches 22 may be based on a first or lower threshold limit being exceeded by a signal generated by any one or more of the proximity sensors. When a proximity sensor associated with one of the proximity switches detects a finger in closer proximity with a higher threshold signal, indicative of an attempted activation of the proximity switch, a switch output may be generated and a feedback lighted output may be generated to illuminate that activated proximity switch to indicate that the proximity switch has been activated. This may include activating the proximity switch or lighting the proximity switch in a red second color, according to one example. If the user 30 performs a wrong touch on one or more of the proximity switches 22 or if an incorrect code is entered in the input sequence, one or more of the proximity switches 22 may be illuminated in a third color, such as amber, for example.

Figure 3:
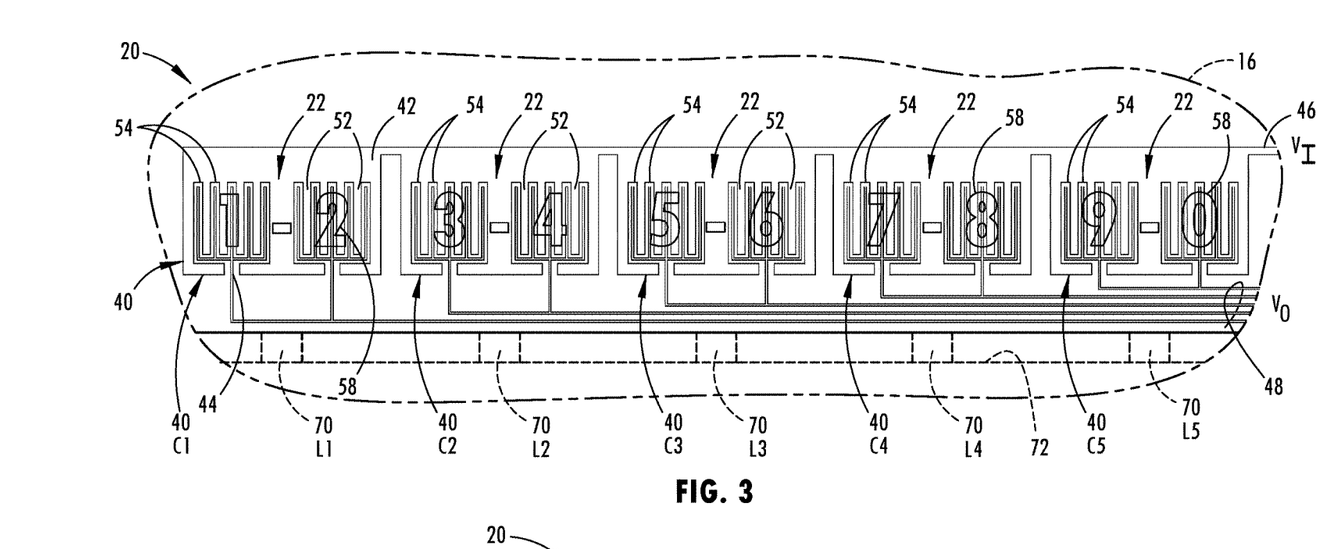
FIG. 3 is a front view of the capacitive proximity switch and moisture sensing assembly shown in FIG. 2 further illustrating the transparent proximity sensors.

The proximity switch and moisture sensing assembly 20 is further illustrated in FIG. 3 in more detail showing five proximity sensors configured as capacitive sensors 40 positioned to sense an object contacting or in close proximity to the corresponding proximity switches 22. In addition, one or more of the proximity sensors associated with one or more of the proximity switches 22 also senses moisture such as humidity or condensation on the interior surface of the glass window 16. Sensed moisture may be in the form of humidity which is water vapor in the air, or may in the form of condensation which is water on a surface which can be in the form of a liquid water or a frozen water (e.g., ice or frost).

As seen in FIG. 3, each of the capacitive sensors 40 includes a first electrode 42 and a second electrode 44. Each of the first and second electrodes 42 and 44 includes a plurality of conductive electrode fingers 52 and 54, respectively. As such, the first electrode 42 has a first plurality of electrode fingers 52 and the second electrode 44 has a second plurality of electrode fingers 54. Each of the first and second electrode plurality of fingers 52 and 54 are generally positioned to be interdigitated or interlaced with the other of the first and second plurality of electrode fingers 52 and 54 to at least some degree to generate a capacitive activation field for sensing the presence of an object such as a user's hand or finger. The first electrode 42 may be configured as a receive electrode and receives a sense signal, and the second electrode 44 may be configured as a drive electrode to receive a drive signal.

The capacitive sensors 40 each provide a capacitive sense activation field to sense contact or close proximity (e.g., within one mm) of a user (e.g., finger) in relation to the corresponding capacitive sensor. The capacitive sense activation field of each capacitive sensor 40 detects a user's finger which has electrical conductivity and dielectric properties that cause a change or disturbance in the capacitive sense activation field as should be evident to those skilled in the art. Each of the capacitive sensors 40 provides a sensed signal for a corresponding proximity switch 22 indicative of a user input. A user may enter a sequence of user inputs on the proximity switches 22 that match a programmed key code to lock or unlock one or more vehicle doors, according to one embodiment.

In addition, one or more of the capacitive sensors 40 is also configured to sense moisture such as condensation on the interior surface of the glass window or humidity proximate the interior surface of the glass window. The sensed moisture may include condensation formed as water vapor on the interior surface of the window. The sensed moisture may also include humidity in the form of water vapor in the air proximate to the interior surface of the vehicle window, such as in the vehicle passenger compartment. The moisture is sensed by a change in the signal generated by the proximity sensor 40 due to the moisture content in the air or on the surface of the interior glass of the window. When moisture is detected, the vehicle may activate a window defogger or other control device in response to the detected moisture level in an attempt to reduce the moisture.

The capacitive sensors 40 each generally have the drive electrode 44 and the receive electrode 42, each having interdigitated fingers for generating a capacitive field. It should be appreciated that each of the capacitive sensors 40 may be formed by printed conductive ink or by assembling preformed conductive circuitry onto a substrate. According to one embodiment, the drive electrode 44 receives square wave drive signal pulses applied at voltage $V_I$. The receive electrode 42 has an output for generating an output voltage $V_O$. It should be appreciated that the electrodes 42 and 44 and electrode fingers 52 and 54 may be arranged in various configurations for generating the capacitive fields as the sense activation fields, according to various embodiments.

The drive electrodes 44 receive drive input signals $V_I$ on drive lines 48. The capacitive sensors 40 have a common output line 46 for outputting the corresponding voltage $V_O$. It should be appreciated that the drive and receive electrodes may be otherwise configured so that other types of single electrode or other multiples of electrode arrangements may be used. The capacitive proximity switch and moisture sensing assembly 20 may advantageously be formed with conductive ink or may alternatively be formed with flex circuitry. The capacitive proximity switch and moisture sensing assembly 20 may be used with various types and sizes of proximity switches and characters.

In the embodiment shown and described herein, the drive electrode 44 of each capacitive sensor 40 is supplied with input voltage $V_I$ as square wave signal pulses having a charge pulse cycle sufficient to charge the receive electrode 42 to a desired voltage. The receive electrode 42 thereby serves as a measurement electrode. The adjacent sense activation fields generated by adjacent capacitive sensors may overlap slightly or overlap may not exist. When a user or operator, such as a user's finger enters a capacitive sense activation field, the corresponding capacitive sensor detects a disturbance caused by the finger to the activation field and determines whether the disturbance is sufficient to generate an input with the corresponding capacitive sensor. Similarly, when moisture, such as humidity or condensation on the interior surface of the glass window is detected, the moisture causes a disturbance in the activation field which generates a signal that is processed to determine the moisture level. The disturbance of the activation field is detected by processing the charge pulse signal associated with the corresponding signal channel for that capacitive sensor. Each capacitive sensor 40 has its own dedicated signal channel generating a distinct charge pulse signal which may be processed individually.

Figure 4:
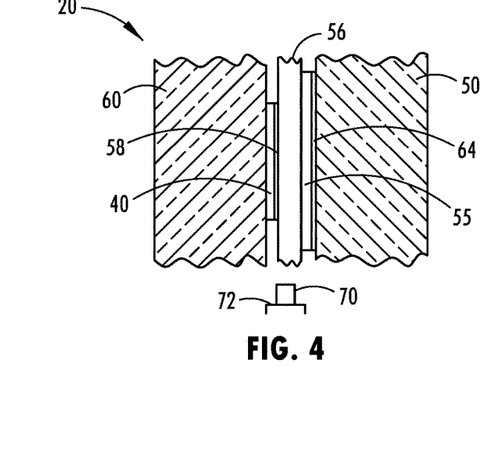
FIG. 4 is a cross-sectional view of the capacitive proximity switch and moisture sensing assembly taken through line IV-IV of FIG. 2, according to one embodiment.
Figure 5:
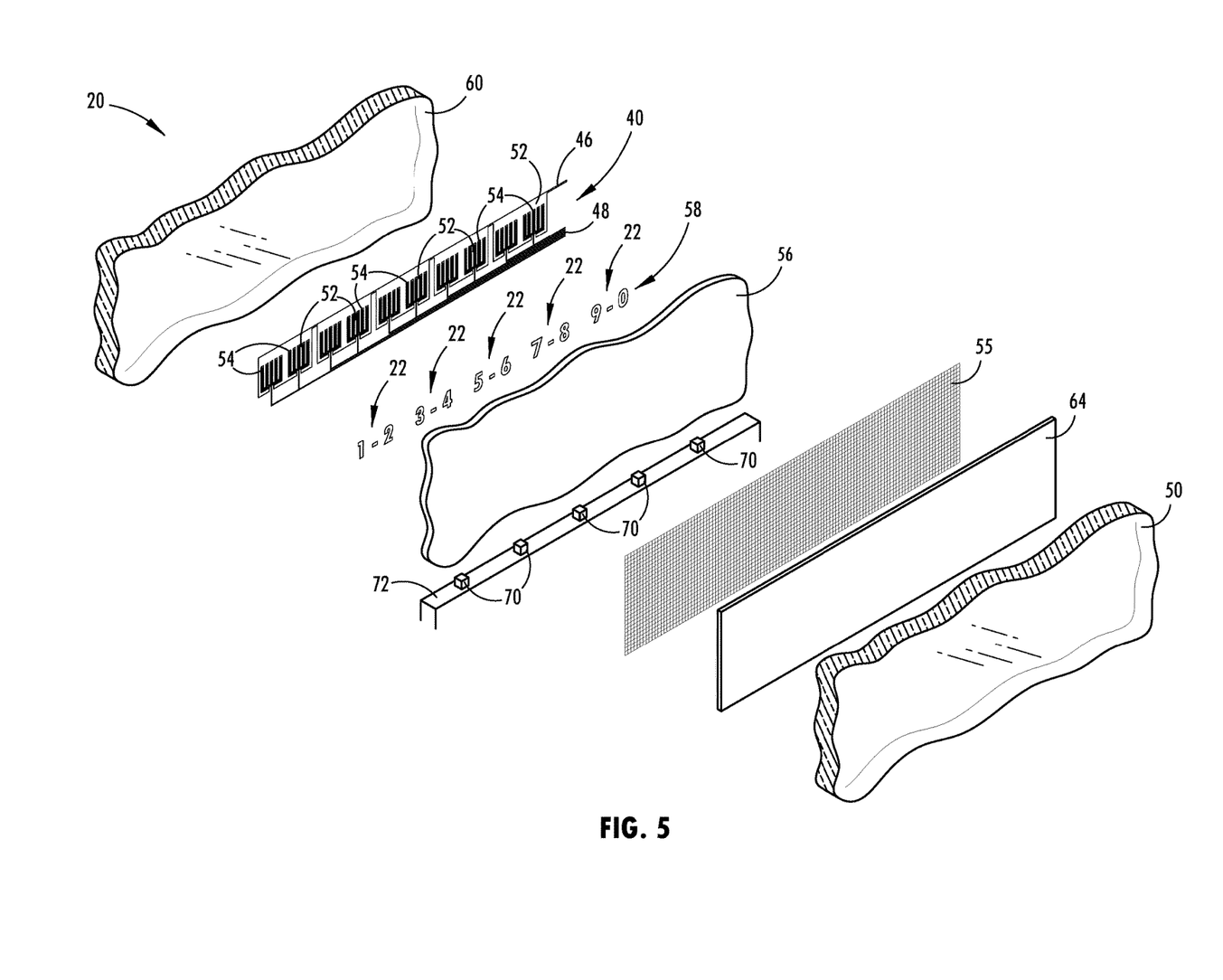
FIG. 5 is an exploded view of the capacitive proximity switch and moisture sensing assembly illustrated in FIG. 4.
Figure 5A:
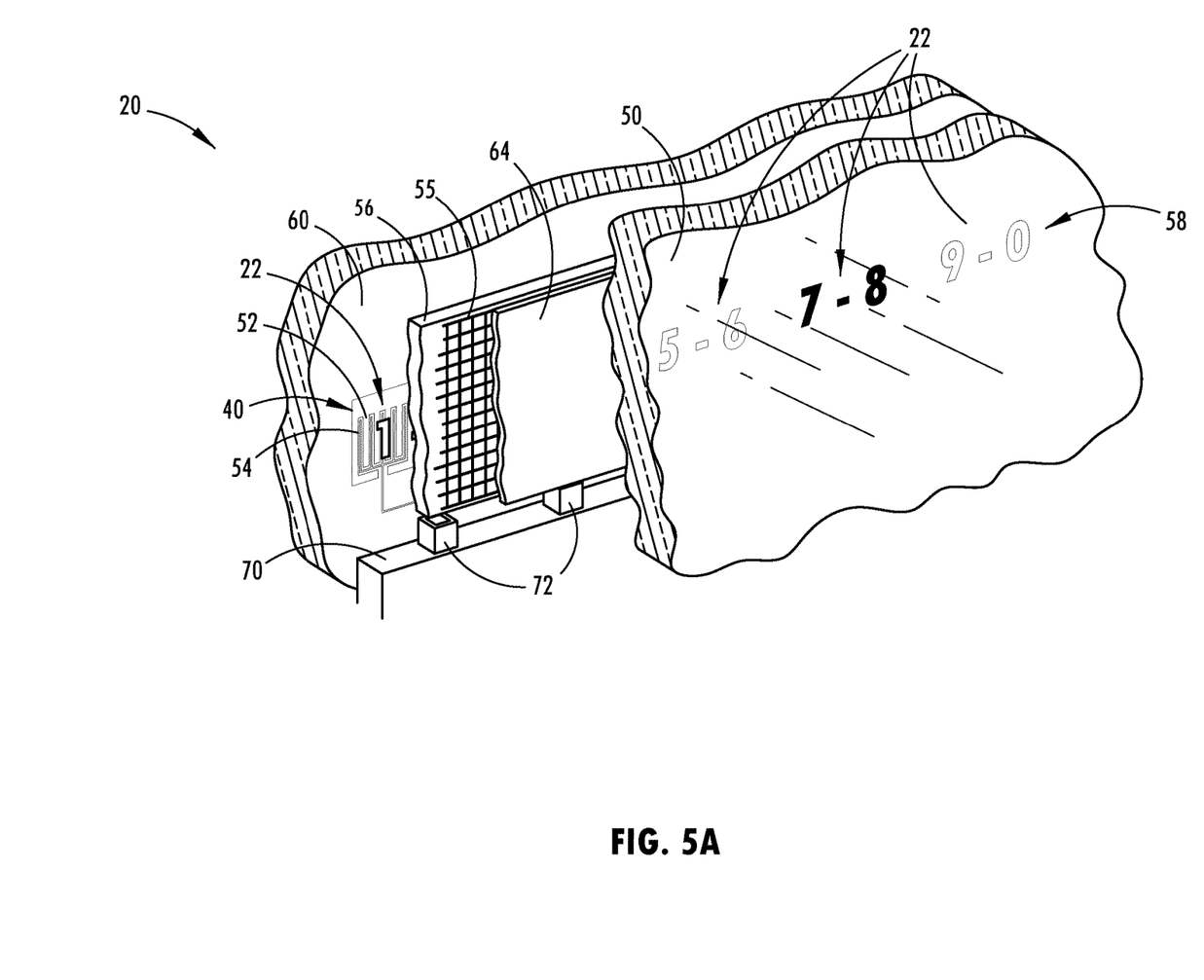
FIG. 5A is an enlarged exploded view of a portion of the proximity switch and moisture assembly of FIG. 5.

Referring to FIGS. 4-5A, the proximity switch and moisture sensing assembly 20 is further shown formed within the glass window 16 sandwiched between the outer glass layer 50 and the inner glass layer 60. The glass window 16 is a visually transparent medium that may serve as a window pane. The transparent medium has a first interior surface and a second exterior surface. It should be appreciated that other visually transparent mediums could be used for the window 16. The proximity switch and moisture assembly 20 includes a transparent dielectric polymeric or plastic layer 56 which may be a polymid layer in the shape of a sheet extending between the outer and inner glass layers 50 and 60. The polymid layer 56 may have a thickness of approximately one millimeter or less, according to one example. The polymid layer 56 is transparent and is light transmissive such that it operates as a light pipe to transmit light emitted from the light sources to the fluorescent patterns or characters 58. Disposed between the polymid layer 56 and the inner glass layer 60 are the proximity sensors 40. The proximity sensors 40 may be formed with a film of indium tin oxide (ITO). The ITO forming the proximity sensors 40 may be formed as an ink printed onto the front surface of the polymid layer 56, according to one embodiment. The ITO may be deposited as a thin film onto the outer surface of the inner glass layer 60 and may have a thickness of about 1000 to 3000 angstroms to form a transparent electrical conductor. The ITO layer forming the proximity sensors 40 is a visually transparent medium that can be used to form the electrodes and signal lines for forming the proximity sensors. As such, the proximity sensors 40 will remain substantially invisible to a user looking through the window 16. In other embodiments, other transparent or semi-transparent or visible conductive inks or films may be used to form the proximity sensors 40.

Disposed between the polymid layer 56 and the proximity sensors 40 on the inner glass layer 60 are the fluorescent characters 58 that may be printed in a fluorescent pattern with a security ink to define characters. The fluorescent pattern may be an ink, such as a security ink, that illuminates visible light when activated by ultraviolet radiation at a wavelength in the range of 200 to 400 nm or infrared radiation at a wavelength in the range of 700 to 1400 nm. It should be appreciated that the fluorescent characters 58 may otherwise be formed on another medium proximate to the polymid layer 56, according to other embodiments. The fluorescent pattern may be formed of a security ink that is a transparent ink that is generally invisible to the eyes of a person except when illuminated by ultraviolet or infrared radiation. The security ink can be printed onto a clear film and then attached to the polymid layer 56 or alternatively can be printed directly onto the polymid layer 56 or etched into the polymid layer 56 in the shape of the character(s).

The fluorescent characters 58 may include up-converting phosphors which are microscopic ceramic powders that convert invisible infrared light wavelengths to visible colored light. The up-converting phosphors exhibit an anti-stokes shift that separates emission peaks from the infrared excitation source. The phosphors light up when illuminated with an infrared light, according to one embodiment. Up-converting phosphors can emit visible green, red, orange or blue colors when illuminated with an infrared illumination. Similarly, UV ink may be employed to form the fluorescent character and is illuminable to a visible light color when illuminated with ultraviolet light. It should be appreciated that both IR and UV illuminable fluorescent inks are commercially available, such as the type used for security ink.

The fluorescent characters 58 are located near a lower edge of the window 16, according to one embodiment. This allows for edge lighting LEDs 70 to be located within the door near the bottom edge of the window 16. The edge lighting LED 70 may be formed on an LED board 72, such as a printed circuit board. Each of the edge lighting LEDs 70 are aligned with one of the proximity switches 22 and the associated fluorescent characters 58. The edge lighting 70 may selectively generate ultraviolet radiation and infrared radiation which is transmitted through the polymid layer 56 to illuminate the fluorescent patterns or characters 58. As such, the edge lighting LEDs 70 are spaced sufficiently apart from one another and aligned so as to generate a light output that illuminates the corresponding fluorescent characters 58 without interfering with other fluorescent characters. As such, certain select LEDs may be illuminated one at a time with either infrared or ultraviolet light to generate a desired color output from the fluorescent characters 58.

In addition to sensing an activation of the proximity switches 22, the proximity switch and moisture sensing assembly 20 also detects the moisture, such as humidity and condensation, on the first interior surface with the use of the one or more proximity sensors 24 associated with the one or more of the proximity switches 22. The proximity sensor 24, configured as a capacitive sensor in the embodiment shown and described herein, is sensitive to moisture which affects the sensor activation field similar to a touch by a user's finger. Unlike a typical touch activation which causes a rather fast rise in the signal count, moisture such as humidity or condensation will cause the signal to rise at a slower rate. For example, when someone opens a vehicle door or window and the humidity rises due to the change in the environmental conditions, the humidity or condensation buildup on the window may be detected by monitoring the change in the activation signal in relation to a look-up table. Thus, activations by a user's finger can be distinguished from the moisture and the sensed signal can be used to generate a moisture value that may be used for other purposes on the vehicle such as by a climate control system to control a window defogger or other control device(s). In one embodiment, a single proximity sensor 24 may be used to determine the moisture. According to another embodiment, a plurality of proximity sensors 24 associated with a plurality of proximity switches 22 may be employed to generate multiple moisture signals which may be averaged to provide an average moisture measurement.

Referring again to FIGS. 4-5A, disposed between the polymid layer 56 and the outer glass layer 50 is a conductive shield 55. As such, the conductive shield 55 is provided between the capacitive sensor 40 and the second exterior surface of the window 16. The conductive shield 55 is provided as an intermediary layer between the capacitive sensors 40 and an outer surface of the glass window to reduce the sensitivity of the proximity sensors 40 to moisture present on or proximate to the outside surface of the outer glass layer 50. As a result, moisture on the second exterior surface of the window 16 is less likely to affect the measurement of moisture on the first interior surface of the window 16. In the embodiment shown, the conductive shield 55 is formed as a conductive grid having a plurality of horizontal and vertical conductive lines arranged in rows and columns. In this embodiment, there are non-conductive spaces between the grid, such that the shielding is a partial shielding. In other embodiments, the conductive shield 55 may be a solid conductive material for providing additional shielding or may be formed with different patterns. The conductive shield 55 may be made of a visually transparent or semi-transparent conductive material such as indium tin oxide (ITO). The conductive shield 55 may be formed as a printed ink printed onto the polymid 56. The conductive shield 55 is located forward of the proximity sensors 40 and is preferably at least as large as the proximity sensors 40 and may be larger than the proximate sensors 40 so as to provide sufficient blocking of the effects of moisture on the outer surface of the glass window 16.

Disposed between the conductive shield 55 and the outer glass layer 50 is a UV/IR blocking layer 64. The UV/IR blocking layer 64 serves to block ultraviolet and infrared radiation from penetrating from outside the vehicle through the window 16 and onto the fluorescent pattern 58 to prevent activation of the fluorescent material by sunlight.

The fluorescent characters 58 on the proximity switches 22 are generally invisible to a person when viewed from outside of the window 16. When a user moves a finger into contact or close proximity to one or more of the proximity switches 22, all of the proximity switches 22 are illuminated in a first green color by activating the UV light source for each of the LEDs 70 to illuminate each of the fluorescent characters 58. When a user further contacts one of the proximity switches to make an activation, the IR light source of the LED lights 70 associated with that corresponding proximity switch is illuminated to illuminate that inputted fluorescent character 58 at that proximity switch 22 to generate a second red color light at that proximity switch 22. If two or more proximity switches 22 are wrongly activated at the same time, both the UV and IR LEDs associated with the activated proximity switches are activated at the same time so as to generate a third amber color light for those input wrongly activated proximity switches. This is because the red and the green light combine together will form the third amber color.

Figure 6:
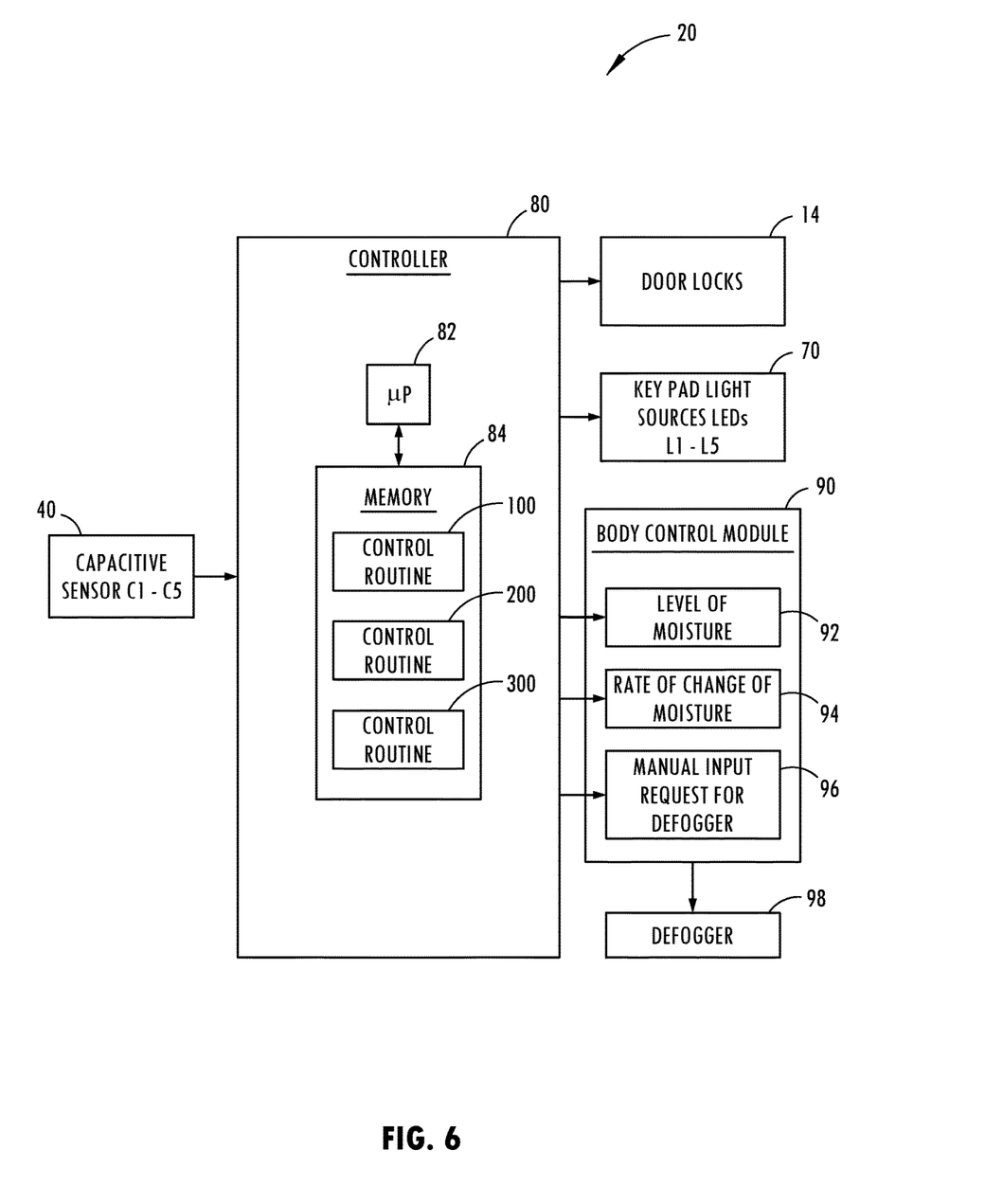
FIG. 6 is a block diagram illustrating controls for processing keypad inputs and sensing moisture and for controlling the door locks, lighting arrangement, and defogger.

Referring to FIG. 6, the proximity switch and moisture sensing assembly 20 is illustrated according to one embodiment. The plurality of capacitive sensors 40 is shown providing respective inputs to a controller 80, such as a microcontroller. The controller 80 may include circuitry, such as a microprocessor 82 and memory 84. The control circuitry may include sense control circuitry processing the activation field of each capacitive sensor to sense user activation by comparing the activation field signal to one or more thresholds pursuant to control routines 100, 200 and 300. It should be appreciated that other analog and/or digital control circuitry may be employed to process each capacitive activation field, to determine user activation, and initiate an action. The controller 80 may employ a Q matrix acquisition method available by ATMEL®, according to one embodiment. Exemplary capacitive sensors are described in the Apr. 9, 2009, ATMEL® Touch Sensors Design Guide 10620 D-AT42-A4/09, the entire reference hereby being incorporated herein by reference.

The controller 80 may include an analog to digital (A/D) comparator integrated within or coupled to the microprocessor 82 which may receive the voltage output $V_O$ from each of the capacitive sensors, convert the analog signal to a digital signal, and provide a digital signal to the microprocessor 82. The controller 80 may include a pulse counter integrated within or coupled to the microprocessor 82 that counts the charge signal pulses that are applied to each drive electrode of each proximity sensor, performs a count of the pulses needed to charge the capacitor until the voltage output $V_O$ reaches a more predetermined voltage, and provides the count to the microprocessor 82. The pulse count is indicative of the change in capacitance of the corresponding capacitive sensor. The controller 80 may provide a pulse width modulated signal to a pulse width modulated drive buffer to generate the square-wave pulse which is applied to each drive electrode of each capacitive sensor. The controller 80 may process the received signals and make a determination as to activation of one of the capacitive sensors and generates one or more signals to activate one or more of the edge lighting LEDS 70 to illuminate UV and/or IR light to one or more of the fluorescent characters 58 to generate a desired color lighting. The controller 80 may further determine whether a sequence of user inputs matches a programmed code and unlock or lock the vehicle door locks 14 when the code is matched by the sequence of inputs. In addition, the controller 80 may further determine the moisture present at or proximate to the interior surface of the glass window and may provide moisture value information to one or more control devices including the body control module 90. The moisture values may include the level of moisture 92 and the rate of change of moisture 94. In addition, a user may manually input a request for defogging of the window 96. The body control module 90 may activate or control one or more devices, such as a window defogger 98 in response to a manual input request for defogging or based on the detected level of moisture 92 or rate of change of moisture 94. A manual input request for defogging 96 may be made by way of a user activating one or more of the proximity switches 22 such as by swiping the user's hand up or down with a gesture input to manual request an increase/decrease of the defogging air flow on the inside surface of the window. The gesture input may be applied to the proximity switches 22 on the first interior surface of the window 16. It should be appreciated that this input or other gesture input requesting manual adjustments of air flow may be used to control a defogging operation.

Figure 7:
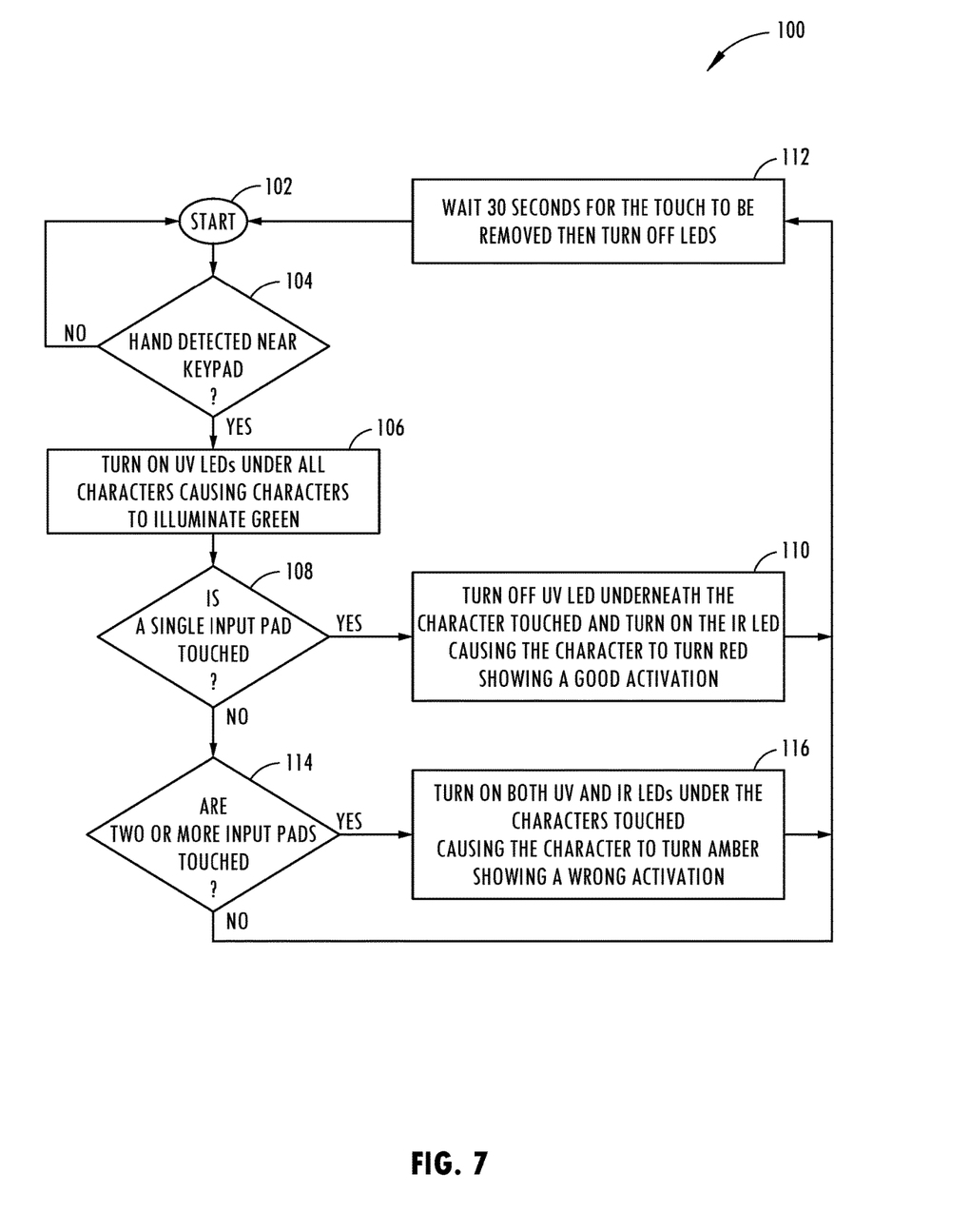
FIG. 7 is a flow chart illustrating a routine for controlling the keypad lighting.

Referring to FIG. 7, the control routine 100 for controlling illumination of the proximity switch assembly is illustrated, according to one embodiment. The control routine 100 starts at step 102 and proceeds to decision step 104 to determine if a hand is detected near the keypad (proximity switches) and, if not, cycles back and waits for a hand detection. Once a hand is detected, routine 100 proceeds to step 106 to turn on the UV edge lighting LEDs under all characters causing the characters to illuminate a green color. Next, at decision step 108, routine 100 determines if a single proximity switch has been touched. If a single proximity switch has been touched, at step 110 routine 100 turns off the UV LED underneath the character touched and turns on the IR LED associated with the touched proximity switch causing the character to turn a red color indicative of good activation. Thereafter, routine 100 waits for a time period such as thirty (30) seconds for the touch to be removed and then turns off the LEDs as step 112 before returning. If a single proximity switch was not touched, routine 100 proceeds to decision step 114 to determine if two or more proximity switches were touched. If two or more proximity switch were touched, routine 100 proceeds to step 116 to turn on both the UV and IR LEDS underneath the characters of the touched proximity switch, thereby causing the characters to turn an amber color indicative of a wrong activation. Thereafter, routine 100 proceeds to step 112 to wait thirty (30) seconds for the touch to be removed and then turns off the LEDs before returning.

Figure 8:
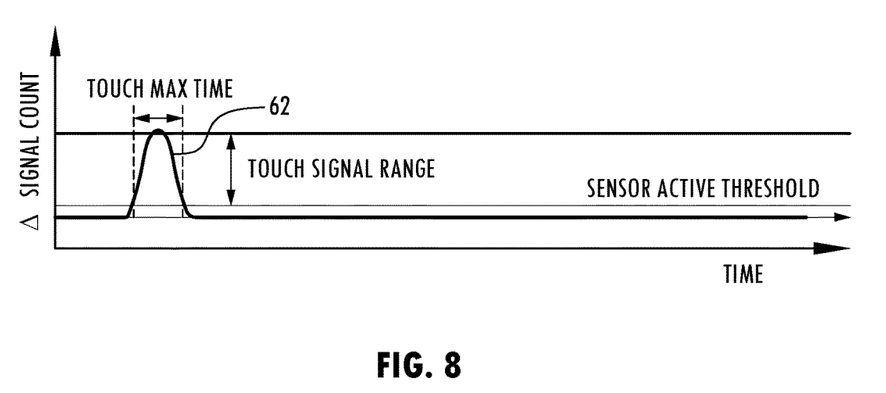
FIG. 8 is a graph illustrating the signal count for one signal channel associated with a capacitive sensor showing an activation motion profile.
Figure 9:
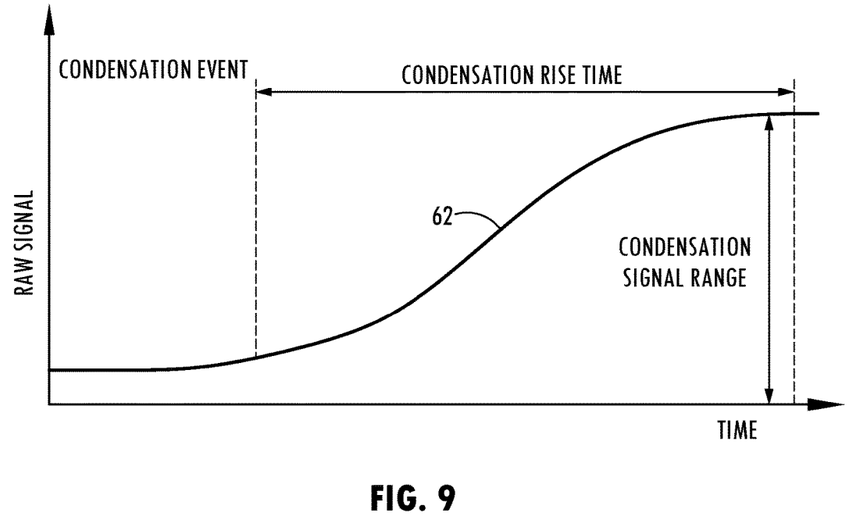
FIG. 9 is a graph illustrating the raw signal for one signal channel associated with the capacitive sensors showing the effect of sensed moisture.
Figure 10:
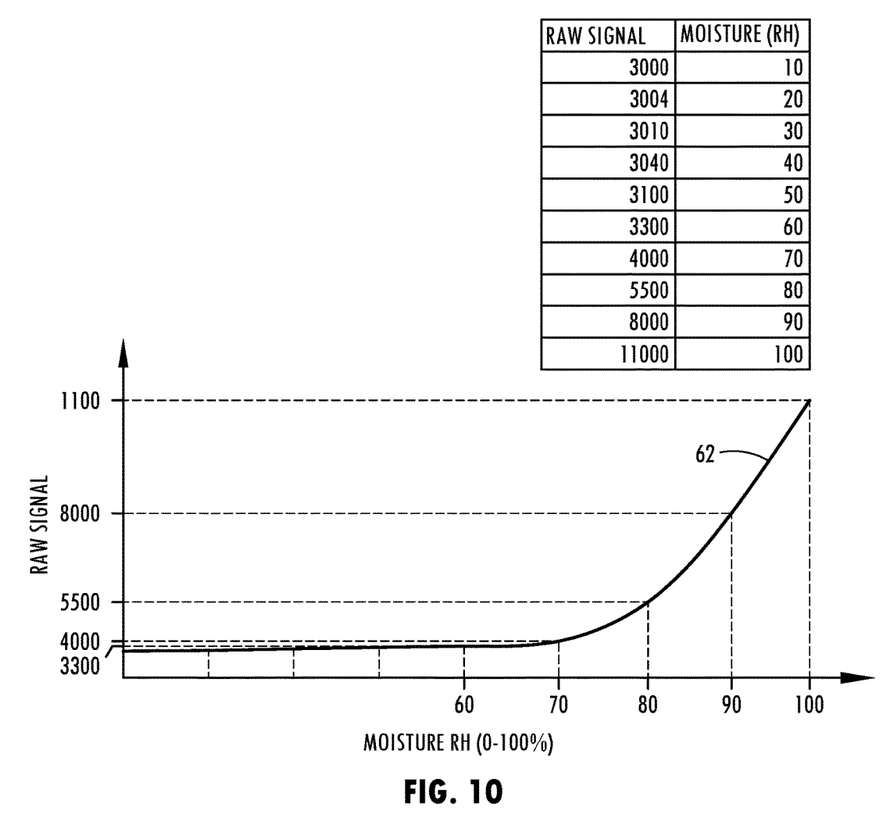
FIG. 10 is a graph illustrating the raw signal for expected moisture values.

In FIGS. 8-10, the change in sensor charge pulse counts shown as signal 62 for a signal channel associated with one of the plurality of proximity switches 22, is illustrated for a touch event in FIG. 8 and is shown as a raw signal for humidity detection in FIGS. 9 and 10, according to one example. The change in signal 62 is the count value difference between an initialized referenced count value without any finger or other object present in the activation field and the corresponding sensor reading with low or no humidity. In the example shown in FIG. 8, the user's finger enters the activation field 32 associated with a proximity switches 22 as the user's finger moves across the proximity switch. The signal 62 is the change (4) in sensor charge pulse count associated with a capacitive sensor 24. In the disclosed embodiment, the proximity sensors 24 are capacitive sensors. When a user's finger is in contact with or close proximity of a sensor 24, the finger alters the capacitance measured at the corresponding sensor 24. The capacitance is in parallel to the untouched sensor pad parasitic capacitance, and as such, measures as an offset. The user or operator induced capacitance is proportional to the user's finger or other body part dielectric constant, the surface exposed to the capacitive pad, and is inversely proportional to the distance of the user's limb to the switch button. According to one embodiment, each sensor is excited with a train of voltage pulses via pulse width modulation (PWM) electronics until the sensor is charged up to a set voltage potential. Such an acquisition method charges the receive electrode to a known voltage potential. The cycle is repeated until the voltage across the measurement capacitor reaches a predetermined voltage. Placing a user's finger on the touch surface of the switch introduces external capacitance that increases the amount of charge transferred each cycle, thereby reducing the total number of cycles required for the measurement capacitance to reach the predetermined voltage. The user's finger causes the change in sensor charge pulse count to increase since this value is based on the initialized reference count minus the sensor reading.

Referring to FIG. 8, as the user's finger approaches a proximity switch 22 associated with the signal channel, the finger enters the activation field associated with the capacitive sensor which causes disruption to the capacitance, thereby resulting in a sensor count increase as shown by signal 62 having a typical touch activation motion profile. During a typical user touch activation, the signal rises relatively quickly to exceed a sensor active threshold and then reaches a peak value and then drops back down below the sensor active threshold. A switch activation may be detected based on the signal exceeding a threshold value and/or based on a rise time of the signal.

Referring to FIG. 9, as moisture in the form of condensation on the inner glass surface or humidity proximate thereto increases, the moisture enters the activation field associated with the capacitive sensor and causes a disruption to the capacitance, thereby resulting in a raw signal increase as shown by signal 62. The effect of the moisture on the sensor generates a raw signal that rises at a slower rate as compared to an activation motion of the user's finger. Accordingly, by monitoring the rise time of the signal and the amplitude of the signal and comparing the signal to known values of moisture, the condensation or humidity can be sensed with the proximity sensor.

FIG. 10 shows an example of the raw signal for a sensor signal affected by moisture (e.g., humidity) and a look-up table that links the raw signal data to the moisture level based on testing. The data in the look-up table may be generated during testing of the assembly to determine the raw signal count for each of a plurality of known moisture levels. The moisture valves between those value listed in the look-up table may be determined using interpolation. During manufacture, a calibration routine may be performed at a known moisture point to calibrate the bias in the scale. Accordingly, by processing the raw signal data generated by the capacitive sensor, the corresponding moisture level may be determined.

Figure 11:
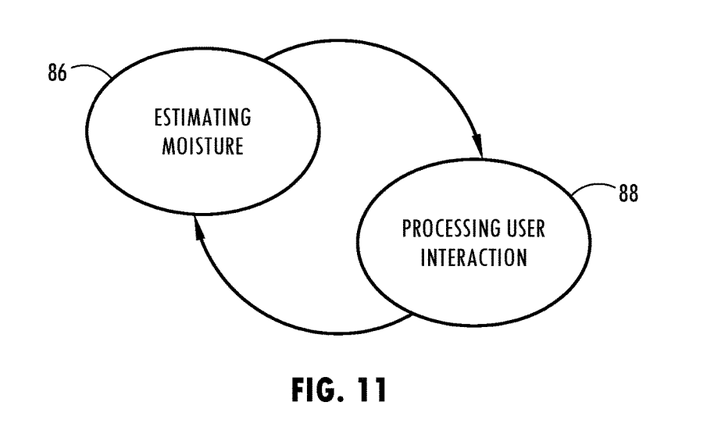
FIG. 11 is a state diagram illustrating switch activation and moisture estimation states for the proximity switch and moisture sensor assembly.

Referring to FIG. 11, the state diagram illustrates two modes of operation that are available with the proximity switch and moisture sensing assembly 20. In a first mode, the assembly 20 may operate in a processing user interaction state 88 to detect the touch of a finger on a switch for a switch activation. In a second mode, the assembly 20 may operate in an estimating moisture state 86 to determine the moisture level. It should be appreciated that the processing user interaction mode 88 may operate during a substantial amount of time, while the estimating moisture mode 88 may periodically be operated. It should be appreciated that the processing user interaction mode 88 and estimating moisture mode 86 could be executed simultaneously.

Figure 12A:
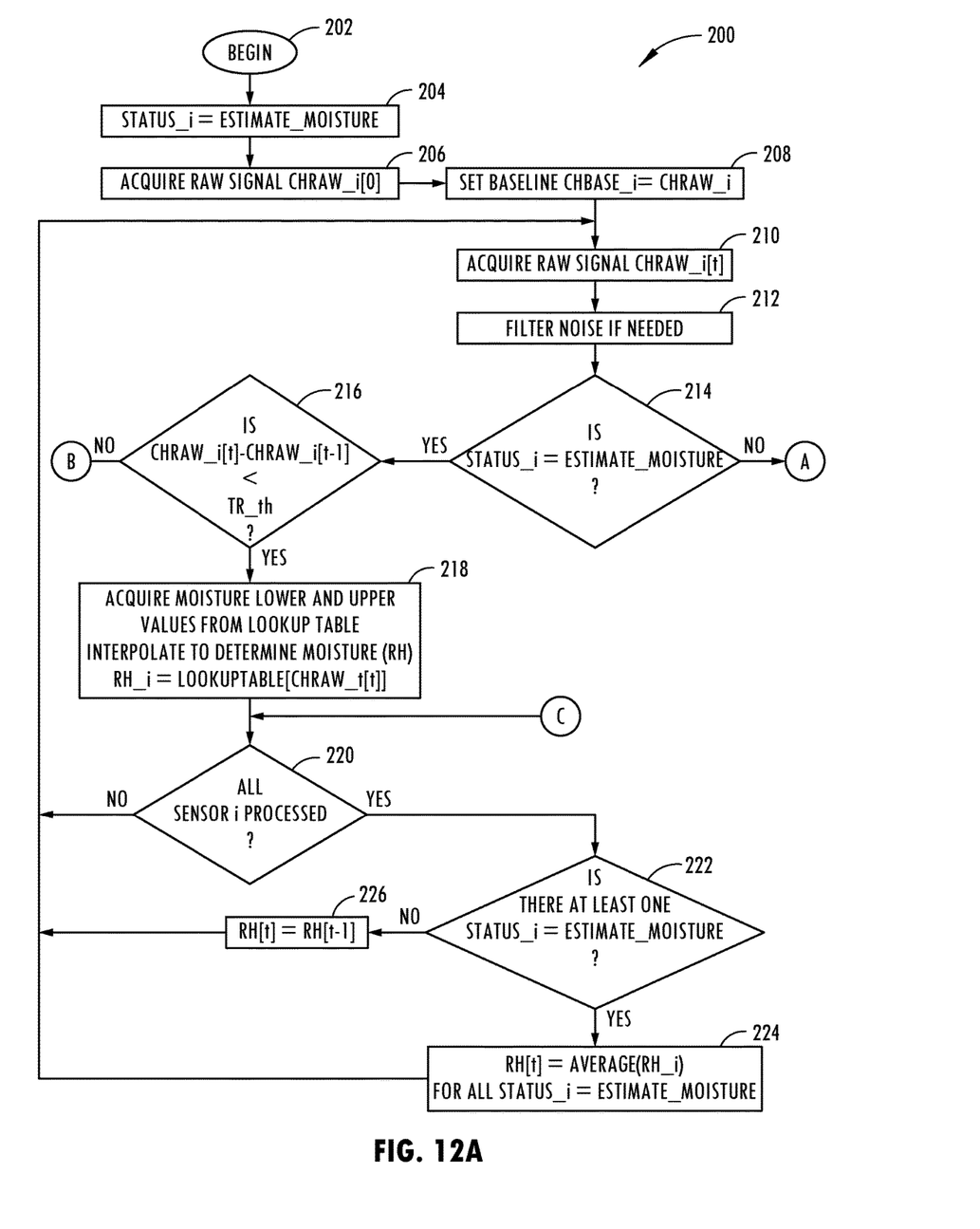
FIGS. 12A and 12B is a flow diagram illustrating a routine for sensing moisture within the vehicle and activating the proximity switch, according to one embodiment.
Figure 12B:
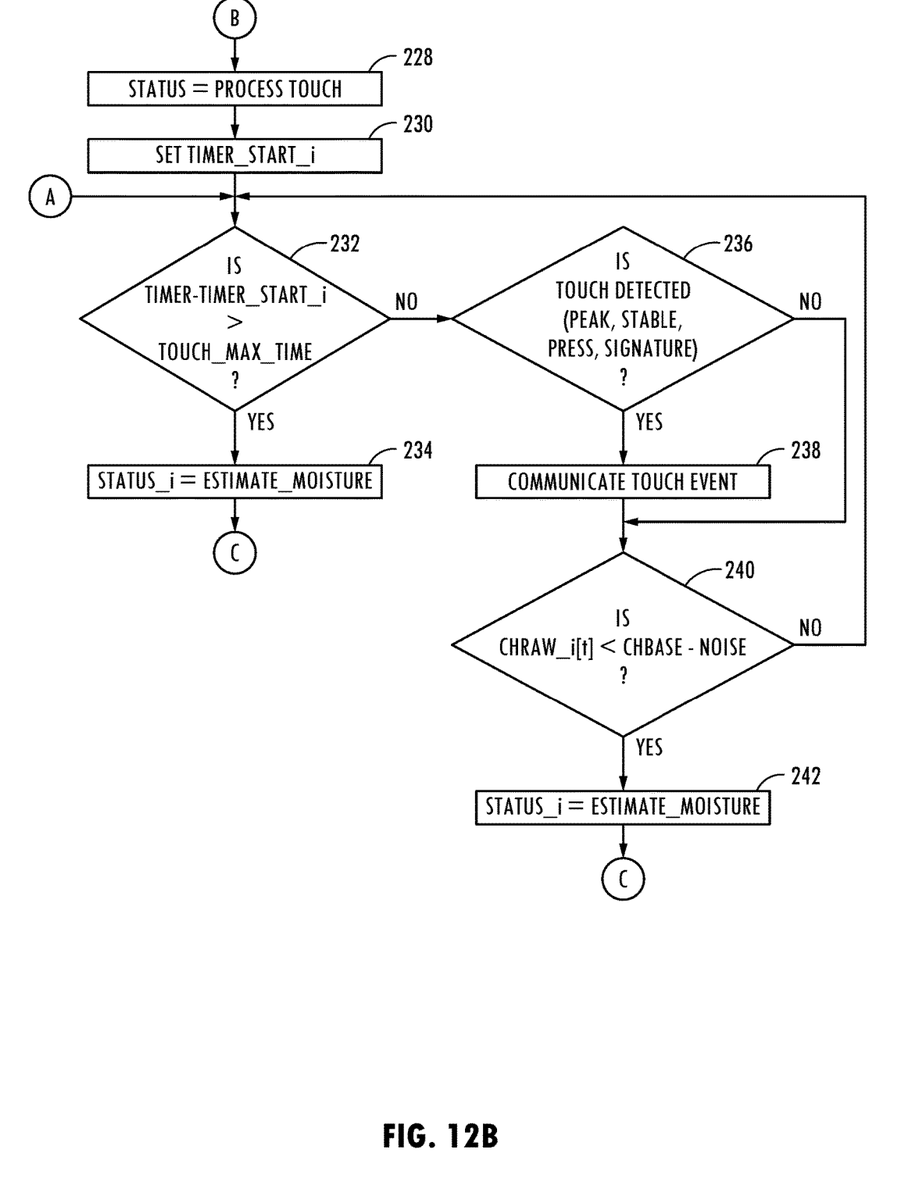

Referring to FIGS. 12A and 12B, a routine 200 for determining switch activation and determining moisture is illustrated, according to one embodiment. The routine 200 begins at step 202 and proceeds to step 204 to set the status state for signal channel (i) to estimate moisture. Next, at step 206 the raw signal CHRAW_i[0] is acquired, and then at step 208 the baseline CHBASE is set equal to the acquired raw signal CHRAW_i. Next, at step 210, the raw signal CHRAWi[t] at the current time (t) is acquired, and noise is filtered in step 212. Proceeding to decision step 214, routine 200 determines if the status_i is set equal to estimate moisture and, if so, proceeds to decision step 216 to determine if the signal is experiencing a slow rise (rate of change in amplitude), that is, if the difference in the current acquired signal i[t] and the previously acquired signal i[t−1] for raw signal CHRAW is less than a threshold TR_th and, if so, proceeds to step 218 to acquire the moisture values for the lower and upper values from the look-up table that define a range containing the value CHRAW[t], and then interpolates to determine the moisture (RH)_i value without that range. Next, at decision step 220, routine 200 determines if all sensors are processed and, if not, returns to step 210. If all sensors i have been processed, routine 200 proceeds to decision step 222 to determine if there is at least one status_i set to estimate moisture and, if not, sets the current moisture value RH([t] equal to the prior moisture value in step 226 and then returns to step 210. Otherwise, if there is at least one status_i set to estimate moisture, then routine 200 determines the moisture value RH[t] equal to an average value of moisture (RH_i) for the sensors i at decision step 224 before returning to step 210. One or more vehicle modules, such as the climate control system, may use the moisture value RH[t] to perform an action, such as turning on or adjusting one or more window defoggers to reduce the effect of moisture on the window.

If the signal experiences a fast rise (rate of change in amplitude) at decision step 216, routine 200 proceeds to step 228 to set the status equal to process touch which is the switch touch mode. Next, a timer is set equal to start_i at step 230, and at decision step 232, routine 200 determines if the timer value minus the timer start_i value exceeds or is greater than a touch_max_time value and, if so, sets the status equal to estimate moisture at step 234 before returning to step 220. If the difference in time does not exceed the touch_max_time, routine 200 proceeds to decision step 236 to determine if a touch has been detected, such as by processing the signal for a peak, a stable signal, a press event, or certain touch signature. If a touch is detected, routine 200 proceeds to step 238 to communicate the existence of the touch event. The touch event may trigger activation of the switch to perform a dedicated function. Otherwise, routine 200 proceeds to decision step 240 to determine if value CHRAWi[t] is less than CHBASE minus noise and, if so, sets the status_i equal to estimate moisture in step 242 before returning to step 220. Otherwise, routine 200 returns to step 232.

Figure 13:
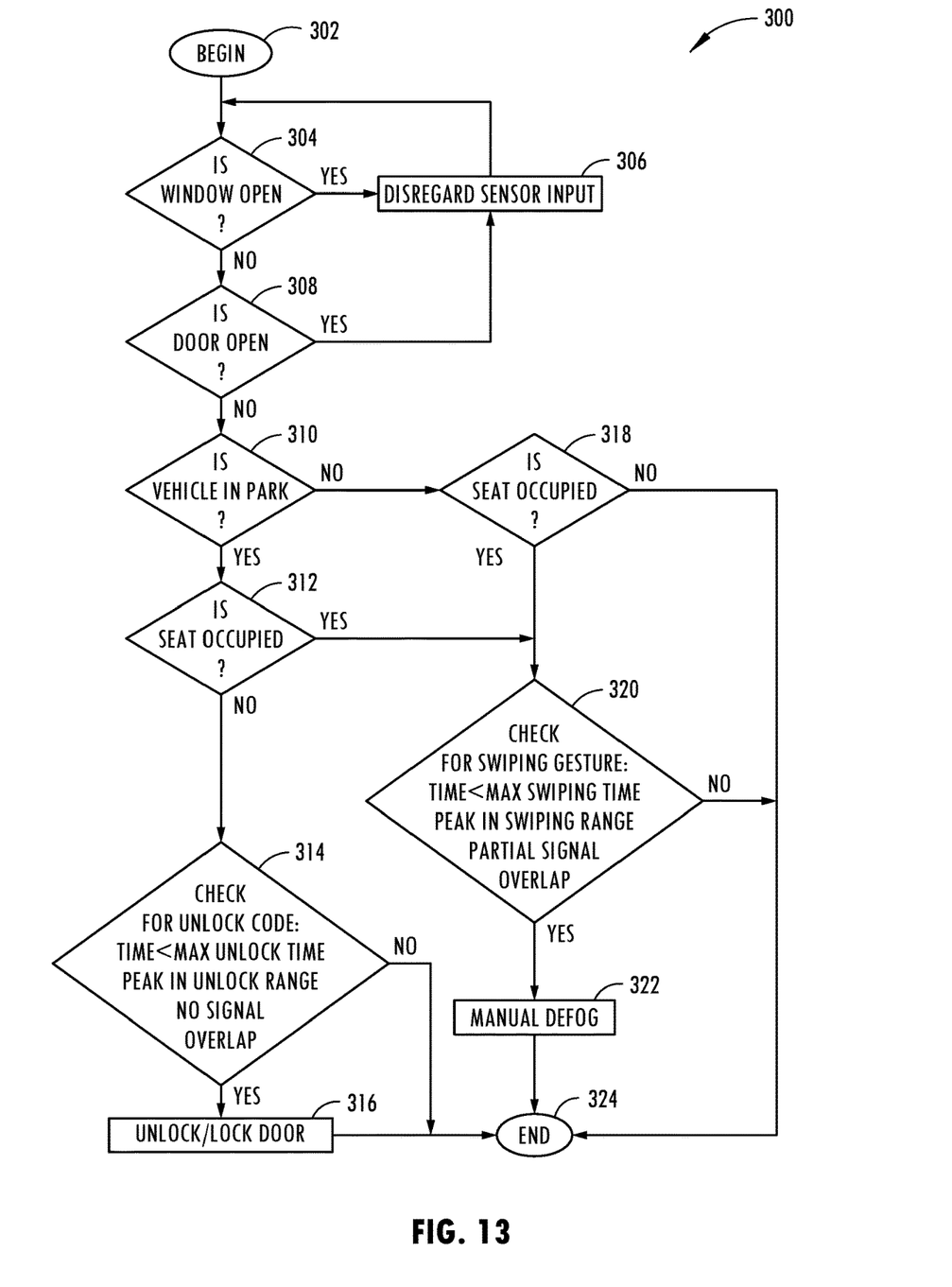
FIG. 13 is a flow chart illustrating a routine for processing the sensor outputs to control vehicle door and window defogging functions, according to one embodiment.

Referring to FIG. 13, a routine 300 is shown for controlling the vehicle and a defogger, according to one embodiment. Routine 300 begins at step 302 and proceeds to decision step 304 to determine if the vehicle window is open. If the vehicle window is open, routine 300 disregards the sensor input at step 306 and returns to step 304. If the vehicle window is not open, routine 300 proceeds to decision step 308 to determine if the door is open and, if so, disregards the sensor input at step 306 and returns to step 304. If the door is not open, routine 300 proceeds to decision step 310 to determine if the vehicle is in park. If the vehicle is in park, routine 300 proceeds to step 312 to determine if the seat is occupied. If the seat is not occupied, indicative of no passenger seated in the vehicle, routine 300 proceeds to decision step 314 to check for the entry of an unlock code with the proximity switches. The unlock code may occur when the time is less than a maximum unlock time, and the peak and the unlock range is detected with no signal overlap. If routine 300 detects an unlock code, routine 300 proceeds to step 316 to perform the unlock/lock door function before ending at step 324. If there is no unlock code, routine 300 proceeds directly to end.

If the vehicle is not in park as detected in decision step 310, routine 300 proceeds to decision step 318 to determine if the seat is occupied and, if not, ends at step 324. If the seat is occupied as detected in either of decision steps 312 and 318, routine 300 proceeds to decision step 320 to check for a swiping gesture input by a passenger in the vehicle to the proximity switches on the interior of the window. The swiping gesture may occur when the time is less than a maximum swiping time and the peak signal is in the swiping range with no partial signal overlap. If a swiping gesture input is detected, routine 300 proceeds to step 322 to activate a manual defogging operation to defog the vehicle window before ending at step 324. If there is no swiping gesture, routine 300 ends at step 324.

The proximity sensors may be manufactured using thin film technology which may include printing a conductive ink mixed with a solvent to achieve a desired electrical circuit layout. The printed ink may be formed into a sheet which is cured in a curing process using controlled heating and light/heat strobing to remove the solvent. Variations in existing curing processes may result in residual solvent trapped in the electrical traces which may result in sensors that are sensitive to changes in temperature and moisture. As condensation builds up on a proximity sensor, the raw capacitive signal and the Δ signal count may change. The condensation buildup may occur in a vehicle, for example, when driving in a rain storm prior to turning on the defroster or when entering the vehicle in a hot, humid summer day. The proximity sensor advantageously detects a user touch activation and moisture using the same sensor. Accordingly, the proximity switch and moisture sensor assembly advantageously provides both proximity sensing for switch activation and moisture measurements.

Accordingly, the proximity switch and moisture sensing assembly 20 advantageously provides for enhanced user activatable proximity switches or input keypads in a window of a vehicle and further provides for enhanced moisture sensing on the interior surface of the vehicle window. Additionally, the assembly 20 provides a moisture sensor that may be employed on a window, such as a vehicle window. It is further conceivable that the assembly 20 may be employed on other windows such as home windows, according to other embodiments. The assembly 20 is substantially transparent when not in use and may be activated in different colors to enable proper operation of the proximity switches and sensing of moisture, such as humidity and condensation on the interior surface of the window. The vehicle operator may further enjoy defogging of the window and may provide manual inputs to control the defogger.

It is to be understood that variations and modifications can be made on the aforementioned structure without departing from the concepts of the present invention, and further it is to be understood that such concepts are intended to be covered by the following claims unless these claims by their language expressly state otherwise.

What is claimed is:

1. A window having moisture sensing, comprising:
   a transparent medium having first and second surfaces;
   a capacitive sensor disposed on the transparent medium for sensing moisture on the first surface; and
   a conductive shield provided between the capacitive sensor and the second surface of the transparent medium, the conductive shield reducing sensitivity of the sensor to moisture on the second surface, wherein the conductive shield is formed of a conductive grid, and wherein the capacitive sensor further operates as a capacitive switch for a keypad assembly to control operation of a door lock to lock or unlock a vehicle door.

2. The window of claim 1, wherein the transparent medium comprises a glass structure.

3. The window of claim 2, wherein the glass structure comprises a first glass layer and a second glass layer, wherein the capacitive sensor is located between the first and second glass layers.

4. The window of claim 3, wherein the conductive grid is disposed between the capacitive sensor and the second glass layer.

5. The window of claim 1, wherein the capacitive sensor senses moisture based on amplitude of a signal.

6. The window of claim 5, wherein the moisture is determined by comparing the amplitude of the signal to known moisture values in a look-up table.

7. The window of claim 1, wherein the window is a vehicle window and the first surface is an interior surface and the second surface is an exterior surface.

8. The window of claim 7 further comprising a defogger for defogging the interior surface of the window based on the sensed moisture.

9. The window of claim 8, wherein control circuitry detects a user gesture input to the sensor and controls the defogger based on the user gesture input.

10. The window of claim 1, wherein the conductive grid comprises an array of horizontal and conductive lines.

11. The window of claim 1, wherein the conductive shield is formed of a substantially transparent conductive material.

12. The window of claim 11, wherein the transparent conductive material comprises indium tin oxide.

13. A vehicle window having moisture sensing, comprising:
   a glass structure having interior and exterior surfaces;
   a capacitive sensor disposed on the glass structure for sensing moisture on the interior surface; and
   a conductive shield provided between the capacitive sensor and the exterior surface of the glass structure, the conductive grid reducing sensitivity of the sensor to moisture on the exterior surface, wherein the conductive shield is formed of a conductive grid, and wherein the capacitive sensor further operates as a capacitive switch for a keypad assembly to control operation of a door lock to lock or unlock a vehicle door.

14. The window of claim 13, wherein the glass structure comprises a first glass layer and a second glass layer, wherein the capacitive sensor is located between the first and second glass layers.

15. The window of claim 14, wherein the capacitive sensor senses moisture based on amplitude of a signal.

16. The window of claim 13, wherein the moisture is determined by comparing the amplitude of the signal to known moisture values in a look-up table.

17. The window of claim 13 further comprising a defogger for defogging the interior surface of the window based on the sensed moisture.

18. The window of claim 13, wherein the conductive grid comprises an array of horizontal and conductive lines.

* * * * *